US006441154B1

(12) United States Patent
Donoho et al.

(10) Patent No.: US 6,441,154 B1
(45) Date of Patent: Aug. 27, 2002

(54) HUMAN PROTEASES AND POLYNUCLEOTIDES ENCODING THE SAME

(75) Inventors: Gregory Donoho, The Woodlands; Erin Hilbun, Spring; C. Alexander Turner, Jr., The Woodlands, all of TX (US); Michael C. Nehls, Stockdorf (DE); Glenn Friedrich, Houston, TX (US); Brian Zambrowicz; Arthur T. Sands, both of The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/710,099

(22) Filed: Nov. 10, 2000

Related U.S. Application Data

(60) Provisional application No. 60/165,260, filed on Nov. 12, 1999.

(51) Int. Cl.$^7$ .............................. C07H 21/04; C12N 9/48
(52) U.S. Cl. ...................................... 536/23.2; 435/212
(58) Field of Search ........................ 536/23.2; 435/212, 435/6

(56) References Cited

U.S. PATENT DOCUMENTS

| | | | |
|---|---|---|---|
| 4,215,051 A | 7/1980 | Schroeder et al. ..... 260/999.999 |
| 4,376,110 A | 3/1983 | David et al. .................... 424/1 |
| 4,594,595 A | 6/1986 | Struckman ................... 343/770 |
| 4,946,778 A | 8/1990 | Ladner et al. ................. 435/69 |
| 5,459,127 A | 10/1995 | Felgner et al. ................. 514/7 |
| 5,474,901 A | 12/1995 | Drayna et al. ............... 435/7.4 |
| 5,593,674 A | 1/1997 | Drayna et al. ............ 424/94.63 |
| 5,837,458 A | 11/1998 | Minshull et al. ................ 435/6 |
| 5,869,336 A | 2/1999 | Meyer et al. ................ 435/348 |
| 5,877,397 A | 3/1999 | Lonberg et al. ............. 800/200 |
| 5,948,767 A | 9/1999 | Scheule et al. ................ 514/44 |
| 6,075,181 A | 6/2000 | Kucherlapati et al. ........ 800/25 |
| 6,110,490 A | 8/2000 | Thierry ....................... 424/450 |

OTHER PUBLICATIONS

Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukayotic Cells", J. Mol. Biol. 150:1–14.
Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.
Greenspan et al. 1993, "Idiotypes: structure and immunogenicity", FASEB Journal 7:437–444.

Huse et al, 1989, "Generation of a Large Combinatorial Library of the Immonoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'-O-methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS USA 88:8972–8976.
Kohler & Milstein, 1975, "Continuous cultures of fused cells secreting antibody of predefined specificity", Nature 256:495–497.
Logan et al, 1984, "Adenovirus tripartite leader sequence enhances translation of mRNAs late after infection", Proc. Natl. Acad. Sci. USA 81:3655–3659.
Lowry et al, 1980, "Isolation of Transforming DNA: Cloning the Hamster aprt Gene", Cell 22:817–823.
Morrison et al, 1984, "Chimeric human antibody molecules: Mouse antigen–binding domains with human constant region domains", Proc. Natl. Acad. Sci. USA 81:6851–6855.
Mulligan & Berg, 1981, "Selection for animal cells that express the *Echerichia coli* gene coding for xanthine–guanine phosphoribosyltransferase", Proc. Natl. Acad. Sci. USA 78(4): 2072–2076.
Neuberger et al, 1984, "Recombinant antibodies possessing novel effector functions", Nature 312:604–608.
Nisonoff, 1991, "Idiotypes: Concepts and Applications", J. of Immunology 147:2429–2438.
O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.
Ruther et al. 1983, "Easy identification of cDNA clones", EMBO Journal 2(10):1791–1794.
Santerre et al, 1984, "Expression of prokaryotic genes for hygromycin B and G418 resistance as dominant–selection markers in mouse L cells", Gene 30:147–156.
Sarin et al. 1988, "Inhibition of acquired immunodeficiency syndrome virus by oligodeoxynucleoside methylphosphonates", Proc. Natl Acad. Sci. USA 85:7448–7451.

(List continued on next page.)

*Primary Examiner*—Ponnathapu Achutamurthy
*Assistant Examiner*—Yong Pak

(57) ABSTRACT

Novel human polynucleotide and polypeptide sequences are disclosed tat can be used in therapeutic, diagnostic, and pharmacogenomic applications.

2 Claims, No Drawings

OTHER PUBLICATIONS

Smith et al, 1983, "Molecular Engineering of the Autographa californica Nulcear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al. 1989, "Binding activities of a repertoire of single immunoglobulin variable domains secreted from *Echerichia coli*", Nature 341:544–546.

Wigler et al, 1980, "Transformation of mammalian cells with an amplifiable dominant–acting gene", Proc. Natl. Acad. Sci. USA 77(6):3567–3570.

Wigler et al, 1977, "Transfer of Purified Herpes Virus Thymidine Kinase Gene to Bultured Mouse Cells", Cell 11:223–232.

Database Aageneseq 'Online! Derwent; accession No. AAW01504, Feb. 26, 1997 Blumenkopf Ta et al.: "Wild–type human pancreatic carboxypeptidase 1" XP002170914 & WO 95 13095 A (Wellcome Found. LTD.) May 18, 1995 pp. 214–216; example 206.

Database Swissprot 'Online! Accession No. P15085, Apr. 1, 1990 Catasus et al.: "Human Carboxypeptidase A1 Precursor 9EC 3.4.17.1)" XP002170915.

Database Swissprot 'Online! Accession No. P00730, Jul. 21, 1986 Le Hueerou et al.: "Bovine Carboxypeptidase A Precursor (EC 3.4.17.1)" XP002170916.

Database Nageneseq 'Online! Derwent; accession No. AAX89285, Sep. 21, 1999 Au–Young J. et al.: "Human regulatory protein HRGP–1 encoding DNA" XP002170917 & WO 99 33870 A (Incyte Pharm Inc:) Jul. 8, 1999.

Hillier et al. EST database—Accession #AA628217. (Mar. 2, 1998).*

Catasus et al. cDNA cloning and sequence analysis of human pancreatic procarboxypeptidase A1. Biochem. J. vol. 287, 299–303. 1992.*

* cited by examiner

HUMAN PROTEASES AND POLYNUCLEOTIDES ENCODING THE SAME

The present application claims the benefit of U.S. Provisional Application No. 60/165,260 which was filed on Nov. 12, 1999 and is herein incorporated by reference in its entirety.

1. INTRODUCTION

The present invention relates to the discovery, identification, and characterization of novel human polynucleotides encoding proteins that share sequence similarity with animal proteases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring and the treatment of physiological disorders.

2. BACKGROUND OF THE INVENTION

Proteases are enzymes that cleave polypeptide sequences. In particular, carboxypeptidases hydrolyze the peptide bonds at the carboxy-terminal end of an amino acid chain, and have been identified in a wide variety of cells and animals. Peptidases have been implicated in a wide variety of cellular functions including, but not limited to, digestion, coagulation, diabetes, prostate cancer, gynecological disorders, neurological disorders, and obesity. Accordingly, peptidases represent key targets/players for the regulation of a variety of physiological processes and pathways.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal proteases, and especially carboxypeptidases. As such, the described NHPs represent a new family of protease-related proteins with a range of homologues and orthologs that transcend phyla and a broad range of species.

The novel human nucleic acid sequences described herein, encode proteins/open reading frames (ORFs) of 351, 314, 436, 399, 351, 314, and 69 amino acids in length (see SEQ ID NOS: 2, 4, 6, 8, 10, 12 and 14 respectively).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP genes (e.g., expression constructs that place the described gene under the control of a strong promoter system), and transgenic animals that express a NHP transgene, or "knock-outs" (which can be conditional) that do not express a functional NHP.

Further, the present invention also relates to processes of identifying compounds that modulate, i.e., act as agonists or antagonists, of NHP expression and/or NHP product activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of several protease ORFs that encode the described NHP amino acid sequences.

5. DETAILED DESCRIPTION OF THE INVENTION

The NHPS, described for the first time herein, are novel proteins that are expressed in, inter alia, human cell lines, and human prostate, testis, and placenta cells. The described sequences were compiled from gene trapped cDNAs and clones isolated from a human testis cDNA library. The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence in deleted; (d) nucleotides that encode chimeric fusion proteins containing all or a portion of a coding region of an NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent identical or similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or the NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods.

For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand can be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished using labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to an endogenous receptor/ligand of a NHP, but can also identify compounds that trigger NHP-mediated activity.

Finally, the NHP products can be used as therapeutics. For example, soluble versions or derivatives of a NHP, or peptides/domains corresponding a NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize NHP function. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and the corresponding deduced amino acid sequences of the described NHPs are presented in the Sequence Listing. The NHP genes were obtained from a human testis cDNA library using probes and/or primers generated from human gene trapped sequence tags. Expression analysis has provided evidence that the described NHPs can be expressed, for example, in a variety of human cell types and that the described NHPs share significant similarity to a variety of proteases, and especially carboxypeptidase A, and particularly A1 or A2, from, inter alia, humans, mice, and rats. Several polymorphisms were identified during this project including a T-to-C transition at, for example, base number 1007 of SEQ ID NO:5 (changing a L to a S), a G-to-T transversion at position 1014 of SEQ ID NO:5 (changing a E to a D), and a translationally silent T-to-C transition at position 1,158 of SEQ ID NO:5. SEQ ID NO: 15 describes a full length NHP ORF with flanking 5' and 3' sequences.

5.2 NHPS and NHP Polypeptides

NHPs, polypeptides, peptide fragments, mutated, truncated, or deleted forms of the NHPS, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease. Several uses and applications for plasma carboxypeptidases similar to those described herein are described in U.S. Pat. No. 5,593,674, the disclosure of which is herein incorporated by reference in its entirety.

The Sequence Listing discloses the amino acid sequences encoded by the described NHP genes. The NHPs have initiator methionines in DNA sequence contexts consistent with a translation initiation site and a hydrophobic signal-like sequence is present near the N-terminal region of the protein. The sequence data presented herein indicate that alternatively spliced forms of the NHPs exist (which may or may not be tissue specific).

The NHP amino acid sequences of the invention include the nucleotide and amino acid sequences presented in the Sequence Listing as well as analogues and derivatives thereof. Further, corresponding NHP homologues from other species are encompassed by the invention. In fact, any NHP protein encoded by the NHP nucleotide sequences described above, are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Also encompassed by the present invention are novel protein constructs engineered in such a way that they facilitate transport of the NHP to the target site, to the desired organ, across the cell membrane and/or to the nucleus where the NHP can exert its function activity. This goal may be achieved by coupling of the NHP to a cytokine or other ligand that would direct the NHP to the target organ and facilitate receptor mediated transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome based delivery systems. Such technologies are described in U.S. Pat. Nos. 4,594,595, 5,459,127, 5,948,767 and 6,110,490 and their respective disclosures which are herein incorporated by reference in their entirety.

A variety of host-expression vector systems can be used to express the NHP nucleotide sequences of the invention. The presently described NHPs are similar to plasma carboxypeptidases and are likely soluble proteins. Where the NHP peptide or polypeptide to be expressed is a soluble NHP protein, or a NHP peptide derived from a substantially nonhydrophobic domain of a NHP, or a truncated or deleted NHP the peptide or polypeptide can be recovered from the culture, i.e., from the host cell in cases where the NHP peptide or polypeptide is not secreted, or from the culture media in cases where the NHP peptide or polypeptide is secreted by the cells. However, such expression systems also encompass engineered host cells that express a NHP, or functional equivalent, in situ, i.e., anchored in the cell membrane. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that can be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to the *E. coli* expression vector pUR278 (Ruther et al., 1983, EMBO J. 2:1791), in which a NHP coding sequence may be ligated individually into the vector in frame with the 1acZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express Foreign genes. The virus grows in *Spodoptera frugiperda* cells. A NHP gene coding sequence may be cloned individually into non-essential regions (for example the polyhedrin gene) of the virus and placed under control of an AcNPV promoter (for example the polyhedrin promoter). Successful insertion of NHP gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Antibodies, and applications are uses thereof, similar to those contemplated herein are described in U.S. Pat. No. 5,474,901 the disclosure of which is herein incorporated by reference in its entirety.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes, as described, below, for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, an NHP peptide (e.g., one corresponding the a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind and activate or neutralize a receptor, cofactor, ligand, or binding partner. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence of SEQ ID NO:5.

2. An isolated nucleic acid molecule comprising a nucleotide sequence that encodes the amino acid sequence shown in SEQ ID NO:6.

* * * * *

SEQUENCE LISTING

<160> NUMBER OF SEQ ID NOS: 15

<210> SEQ ID NO 1
<211> LENGTH: 1056
<212> TYPE: DNA
<213> ORGANISM: homo sapiens

<400> SEQUENCE: 1

```
atgcagggca ccctggagg cgggacgcgc cctgggccat ccccgtgga caggcggaca      60 ctcctggtct tcagctttat cctggcagca gctttgggcc aaatgaattt cacagggac    120 caggttcttc gagtcctggc caaagatgag aagcagcttt cacttctcgg ggatctggag   180
ggcctgaaac cccagaaggt ggacttctgg cgtggcccag ccaggcccag cctccctgtg   240
gatatgagag ttcctttctc tgaactgaaa gacatcaaag cttatctgga gtctcatgga   300
cttgcttaca gcatcatgat aaaggacatc caggtgctgc tggatgagga aagacaggcc   360 atgcgaaat cccgccggct ggagcgcagc accaacagct tcagttactc atcataccac    420
accctggagg agatatatag ctggattgac aactttgtaa tggagcattc cgatattgtc   480
tcaaaaattc agattggcaa cagctttgaa aaccagtcca ttcttgtcct gaagttcagc   540
actggaggtt ctcggcaccc agccatctgg atcgacactg gaattcactc ccgggagtgg   600
atcacccatg ccaccggcat ctggactgcc aataagattg tcagtgatta tggcaaagac   660
cgtgtcctga cagacatact gaatgccatg gacatcttca tagagctcgt cacaaaccct   720
gatgggtttg cttttaccca cagcatgaac cgcttatggc ggaagaacaa gtccatcaga   780
cctggaatct tctgcatcgg cgtggatctc aacaggaact ggaagtcggg ttttggagga   840
aatggttcta acagcaaccc ctgctcagaa acttatcacg ggccctcccc tcagtcggag   900
ccggaggtgg ctgccatagt gaacttcatc acagcccatg gcaacttcaa ggctctgatc   960
tccatccaca gctactctca gatgcttatg taccccttacg gccgattgct ggagcccgtt  1020
```

-continued

```
tcaaatcaga gggagttggt gagactggct gcttag                    1056
```

<210> SEQ ID NO 2
<211> LENGTH: 351
<212> TYPE: PRT
<213> ORGANISM: homo sapiens

<400> SEQUENCE: 2

```
Met Gln Gly Thr Pro Gly Gly Thr Arg Pro Gly Pro Ser Pro Val
 1               5                  10                  15

Asp Arg Arg Thr Leu Leu Val Phe Ser Phe Ile Leu Ala Ala Ala Leu
                20                  25                  30

Gly Gln Met Asn Phe Thr Gly Asp Gln Val Leu Arg Val Leu Ala Lys
            35                  40                  45

Asp Glu Lys Gln Leu Ser Leu Leu Gly Asp Leu Glu Gly Leu Lys Pro
 50                  55                  60

Gln Lys Val Asp Phe Trp Arg Gly Pro Ala Arg Pro Ser Leu Pro Val
 65                  70                  75                  80

Asp Met Arg Val Pro Phe Ser Glu Leu Lys Asp Ile Lys Ala Tyr Leu
                 85                  90                  95

Glu Ser His Gly Leu Ala Tyr Ser Ile Met Ile Lys Asp Ile Gln Val
                100                 105                 110

Leu Leu Asp Glu Glu Arg Gln Ala Met Ala Lys Ser Arg Arg Leu Glu
            115                 120                 125

Arg Ser Thr Asn Ser Phe Ser Tyr Ser Ser Tyr His Thr Leu Glu Glu
    130                 135                 140

Ile Tyr Ser Trp Ile Asp Asn Phe Val Met Glu His Ser Asp Ile Val
145                 150                 155                 160

Ser Lys Ile Gln Ile Gly Asn Ser Phe Glu Asn Gln Ser Ile Leu Val
                165                 170                 175

Leu Lys Phe Ser Thr Gly Gly Ser Arg His Pro Ala Ile Trp Ile Asp
            180                 185                 190

Thr Gly Ile His Ser Arg Glu Trp Ile Thr His Ala Thr Gly Ile Trp
        195                 200                 205

Thr Ala Asn Lys Ile Val Ser Asp Tyr Gly Lys Asp Arg Val Leu Thr
    210                 215                 220

Asp Ile Leu Asn Ala Met Asp Ile Phe Ile Glu Leu Val Thr Asn Pro
225                 230                 235                 240

Asp Gly Phe Ala Phe Thr His Ser Met Asn Arg Leu Trp Arg Lys Asn
                245                 250                 255

Lys Ser Ile Arg Pro Gly Ile Phe Cys Ile Gly Val Asp Leu Asn Arg
            260                 265                 270

Asn Trp Lys Ser Gly Phe Gly Gly Asn Gly Ser Asn Ser Asn Pro Cys
        275                 280                 285

Ser Glu Thr Tyr His Gly Pro Ser Pro Gln Ser Glu Pro Glu Val Ala
    290                 295                 300

Ala Ile Val Asn Phe Ile Thr Ala His Gly Asn Phe Lys Ala Leu Ile
305                 310                 315                 320

Ser Ile His Ser Tyr Ser Gln Met Leu Met Tyr Pro Tyr Gly Arg Leu
                325                 330                 335

Leu Glu Pro Val Ser Asn Gln Arg Glu Leu Val Arg Leu Ala Ala
            340                 345                 350
```

<210> SEQ ID NO 3
<211> LENGTH: 945

```
<212> TYPE: DNA
<213> ORGANISM: homo sapiens

<400> SEQUENCE: 3 atgcaggggca ccctggagg cgggacgcgc cctgggccat ccccgtgga caggcggaca      60
ctcctggtct tcagctttat cctggcagca gctttgggcc aaatgaattt cacaggggac    120
caggttcttc gagtcctggc caaagatgag aagcagcttt cacttctcgg ggatctggag    180
ggcctgaaac cccagaaggt ggacttctgg cgtggcccag ccaggcccag cctccctgtg    240
gatatgagag ttcctttctc tgaactgaaa gacatcaaag cttatctgga gtctcatgga    300
cttgcttaca gcatcatgat aaaggacatc caggtgctgc tggatgagga agacaggcc     360
atggcgaaat cccgccggct ggagcgcagc accaacagct tcagttactc atcataccac    420
accctggagg agatatatag ctggattgac aactttgtaa tggagcattc cgatattgtc    480
tcaaaaattc agattggcaa cagctttgaa accagtcca ttcttgtcct gaagttcagc     540
actggaggtt ctcggcaccc agccatctgg atcgacactg gaattcactc ccgggagtgg    600
atcacccatg ccaccggcat ctggactgcc aataagaacc gcttatggcg aagaacaag    660
tccatcagac tggaatcttt ctgcatcggc gtggatctca acaggaactg gaagtcgggt    720
tttggaggaa atggttctaa cagcaacccc tgctcagaaa cttatcacgg ccctcccct   780
cagtcggagc cggaggtggc tgccatagtg aacttcatca cagcccatgg caacttcaag    840
gctctgatct ccatccacag ctactctcag atgcttatgt acccttacgg ccgattgctg    900
gagcccgttt caaatcagag ggagttggtg agactggctg cttag                    945

<210> SEQ ID NO 4
<211> LENGTH: 314
<212> TYPE: PRT
<213> ORGANISM: homo sapiens

<400> SEQUENCE: 4

Met Gln Gly Thr Pro Gly Gly Thr Arg Pro Gly Pro Ser Pro Val
 1               5                  10                  15

Asp Arg Arg Thr Leu Leu Val Phe Ser Phe Ile Leu Ala Ala Ala Leu
                20                  25                  30

Gly Gln Met Asn Phe Thr Gly Asp Gln Val Leu Arg Val Leu Ala Lys
            35                  40                  45

Asp Glu Lys Gln Leu Ser Leu Leu Gly Asp Leu Glu Gly Leu Lys Pro
        50                  55                  60

Gln Lys Val Asp Phe Trp Arg Gly Pro Ala Arg Pro Ser Leu Pro Val
 65                  70                  75                  80

Asp Met Arg Val Pro Phe Ser Glu Leu Lys Asp Ile Lys Ala Tyr Leu
                85                  90                  95

Glu Ser His Gly Leu Ala Tyr Ser Ile Met Ile Lys Asp Ile Gln Val
            100                 105                 110

Leu Leu Asp Glu Glu Arg Gln Ala Met Ala Lys Ser Arg Arg Leu Glu
        115                 120                 125

Arg Ser Thr Asn Ser Phe Ser Tyr Ser Ser Tyr His Thr Leu Glu Glu
    130                 135                 140

Ile Tyr Ser Trp Ile Asp Asn Phe Val Met Glu His Ser Asp Ile Val
145                 150                 155                 160

Ser Lys Ile Gln Ile Gly Asn Ser Phe Glu Asn Gln Ser Ile Leu Val
                165                 170                 175

Leu Lys Phe Ser Thr Gly Gly Ser Arg His Pro Ala Ile Trp Ile Asp
```

```
                    180              185              190
Thr Gly Ile His Ser Arg Glu Trp Ile Thr His Ala Thr Gly Ile Trp
            195              200              205
Thr Ala Asn Lys Asn Arg Leu Trp Arg Lys Asn Lys Ser Ile Arg Pro
        210              215              220
Gly Ile Phe Cys Ile Gly Val Asp Leu Asn Arg Asn Trp Lys Ser Gly
225              230              235              240
Phe Gly Gly Asn Gly Ser Asn Ser Asn Pro Cys Ser Glu Thr Tyr His
                245              250              255
Gly Pro Ser Pro Gln Ser Glu Pro Glu Val Ala Ala Ile Val Asn Phe
            260              265              270
Ile Thr Ala His Gly Asn Phe Lys Ala Leu Ile Ser Ile His Ser Tyr
        275              280              285
Ser Gln Met Leu Met Tyr Pro Tyr Gly Arg Leu Leu Glu Pro Val Ser
    290              295              300
Asn Gln Arg Glu Leu Val Arg Leu Ala Ala
305              310

<210> SEQ ID NO 5
<211> LENGTH: 1311
<212> TYPE: DNA
<213> ORGANISM: homo sapiens

<400> SEQUENCE: 5 atgcaggggca cccctggagg cgggacgcgc cctgggccat ccccgtgga caggcggaca      60
ctcctggtct tcagctttat cctggcagca gctttgggcc aaatgaattt cacaggggac     120
caggttcttc gagtcctggc caaagatgag aagcagcttt cacttctcgg ggatctggag     180
ggcctgaaac cccagaaggt ggacttctgg cgtggcccag ccaggccag cctccctgtg      240
gatatgagag ttcctttctc tgaactgaaa gacatcaaag cttatctgga gtctcatgga     300
cttgcttaca gcatcatgat aaaggacatc caggtgctgc tggatgagga agacaggcc      360
atggcgaaat cccgccggct ggagcgcagc accaacagct tcagttactc atcataccac     420
accctggagg agatatatag ctggattgac aactttgtaa tggagcattc cgatattgtc     480
tcaaaaattc agattggcaa cagctttgaa accagtcca ttcttgtcct gaagttcagc      540
actggaggtt ctcggcaccc agccatctgg atcgacactg gaattcactc ccgggagtgg     600
atcacccatg ccaccggcat ctggactgcc aataagattg tcagtgatta tgcaaagac      660
cgtgtcctga cagacatact gaatgccatg gacatcttca tagagctcgt cacaaaccct    720
gatgggtttg cttttaccca cagcatgaac cgcttatggc ggaagaacaa gtccatcaga    780
cctggaatct tctgcatcgg cgtggatctc aacaggaact ggaagtcggg ttttggagga    840
aatggttcta acagcaaccc tgctcagaa acttatcacg gcccctcccc tcagtcggag     900
ccggaggtgg ctgccatagt gaacttcatc acagcccatg gcaacttcaa ggctctgatc    960
tccatccaca gctactctca gatgcttatg taccccttacg gccgattgct ggagcccgtt   1020
tcaaatcaga gggagttgta cgatcttgcc aaggatgcgg tggaggcctt gtataaggtc   1080
catgggatcg agtacatttt tggcagcatc agcaccaccc tctatgtggc cagtgggatc   1140
accgtcgact gggcctatga cagtggcatc aagtacgcct tcagctttga gctccgggac   1200
actgggcagt atggcttcct gctgccggcc acacagatca tccccacggc ccaggagacg   1260
tggatggcgc ttcggaccat catggagcac accctgaatc cccctacta g              1311
```

-continued

```
<210> SEQ ID NO 6
<211> LENGTH: 436
<212> TYPE: PRT
<213> ORGANISM: homo sapiens

<400> SEQUENCE: 6
```

| | | | | | | | | | | | | | | | |
|---|---|---|---|---|---|---|---|---|---|---|---|---|---|---|---|
| Met | Gln | Gly | Thr | Pro | Gly | Gly | Thr | Arg | Pro | Gly | Pro | Ser | Pro | Val | |
| 1 | | | | 5 | | | | | 10 | | | | | 15 | |
| Asp | Arg | Arg | Thr | Leu | Leu | Val | Phe | Ser | Phe | Ile | Leu | Ala | Ala | Ala | Leu |
| | | | 20 | | | | | 25 | | | | | 30 | | |
| Gly | Gln | Met | Asn | Phe | Thr | Gly | Asp | Gln | Val | Leu | Arg | Val | Leu | Ala | Lys |
| | | 35 | | | | | 40 | | | | | 45 | | | |
| Asp | Glu | Lys | Gln | Leu | Ser | Leu | Leu | Gly | Asp | Leu | Glu | Gly | Leu | Lys | Pro |
| | 50 | | | | | 55 | | | | | 60 | | | | |
| Gln | Lys | Val | Asp | Phe | Trp | Arg | Gly | Pro | Ala | Arg | Pro | Ser | Leu | Pro | Val |
| 65 | | | | | 70 | | | | | 75 | | | | | 80 |
| Asp | Met | Arg | Val | Pro | Phe | Ser | Glu | Leu | Lys | Asp | Ile | Lys | Ala | Tyr | Leu |
| | | | | 85 | | | | | 90 | | | | | 95 | |
| Glu | Ser | His | Gly | Leu | Ala | Tyr | Ser | Ile | Met | Ile | Lys | Asp | Ile | Gln | Val |
| | | | 100 | | | | | 105 | | | | | 110 | | |
| Leu | Leu | Asp | Glu | Glu | Arg | Gln | Ala | Met | Ala | Lys | Ser | Arg | Arg | Leu | Glu |
| | | 115 | | | | | 120 | | | | | 125 | | | |
| Arg | Ser | Thr | Asn | Ser | Phe | Ser | Tyr | Ser | Ser | Tyr | His | Thr | Leu | Glu | Glu |
| | 130 | | | | | 135 | | | | | 140 | | | | |
| Ile | Tyr | Ser | Trp | Ile | Asp | Asn | Phe | Val | Met | Glu | His | Ser | Asp | Ile | Val |
| 145 | | | | | 150 | | | | | 155 | | | | | 160 |
| Ser | Lys | Ile | Gln | Ile | Gly | Asn | Ser | Phe | Glu | Asn | Gln | Ser | Ile | Leu | Val |
| | | | | 165 | | | | | 170 | | | | | 175 | |
| Leu | Lys | Phe | Ser | Thr | Gly | Gly | Ser | Arg | His | Pro | Ala | Ile | Trp | Ile | Asp |
| | | | 180 | | | | | 185 | | | | | 190 | | |
| Thr | Gly | Ile | His | Ser | Arg | Glu | Trp | Ile | Thr | His | Ala | Thr | Gly | Ile | Trp |
| | | 195 | | | | | 200 | | | | | 205 | | | |
| Thr | Ala | Asn | Lys | Ile | Val | Ser | Asp | Tyr | Gly | Lys | Asp | Arg | Val | Leu | Thr |
| | 210 | | | | | 215 | | | | | 220 | | | | |
| Asp | Ile | Leu | Asn | Ala | Met | Asp | Ile | Phe | Ile | Glu | Leu | Val | Thr | Asn | Pro |
| 225 | | | | | 230 | | | | | 235 | | | | | 240 |
| Asp | Gly | Phe | Ala | Phe | Thr | His | Ser | Met | Asn | Arg | Leu | Trp | Arg | Lys | Asn |
| | | | | 245 | | | | | 250 | | | | | 255 | |
| Lys | Ser | Ile | Arg | Pro | Gly | Ile | Phe | Cys | Ile | Gly | Val | Asp | Leu | Asn | Arg |
| | | | 260 | | | | | 265 | | | | | 270 | | |
| Asn | Trp | Lys | Ser | Gly | Phe | Gly | Gly | Asn | Gly | Ser | Asn | Ser | Asn | Pro | Cys |
| | | 275 | | | | | 280 | | | | | 285 | | | |
| Ser | Glu | Thr | Tyr | His | Gly | Pro | Ser | Pro | Gln | Ser | Glu | Pro | Glu | Val | Ala |
| | 290 | | | | | 295 | | | | | 300 | | | | |
| Ala | Ile | Val | Asn | Phe | Ile | Thr | Ala | His | Gly | Asn | Phe | Lys | Ala | Leu | Ile |
| 305 | | | | | 310 | | | | | 315 | | | | | 320 |
| Ser | Ile | His | Ser | Tyr | Ser | Gln | Met | Leu | Met | Tyr | Pro | Tyr | Gly | Arg | Leu |
| | | | | 325 | | | | | 330 | | | | | 335 | |
| Leu | Glu | Pro | Val | Ser | Asn | Gln | Arg | Glu | Leu | Tyr | Asp | Leu | Ala | Lys | Asp |
| | | | 340 | | | | | 345 | | | | | 350 | | |
| Ala | Val | Glu | Ala | Leu | Tyr | Lys | Val | His | Gly | Ile | Glu | Tyr | Ile | Phe | Gly |
| | | 355 | | | | | 360 | | | | | 365 | | | |
| Ser | Ile | Ser | Thr | Thr | Leu | Tyr | Val | Ala | Ser | Gly | Ile | Thr | Val | Asp | Trp |
| | 370 | | | | | 375 | | | | | 380 | | | | |

```
Ala Tyr Asp Ser Gly Ile Lys Tyr Ala Phe Ser Phe Glu Leu Arg Asp
385                 390                 395                 400

Thr Gly Gln Tyr Gly Phe Leu Leu Pro Ala Thr Gln Ile Ile Pro Thr
            405                 410                 415

Ala Gln Glu Thr Trp Met Ala Leu Arg Thr Ile Met Glu His Thr Leu
        420                 425                 430

Asn His Pro Tyr
        435

<210> SEQ ID NO 7
<211> LENGTH: 1200
<212> TYPE: DNA
<213> ORGANISM: homo sapiens

<400> SEQUENCE: 7
atgcagggca cccctggagg cgggacgcgc cctgggccat ccccgtgga caggcggaca      60 ctcctggtct tcagctttat cctggcagca gctttgggcc aaatgaattt cacaggggac     120
caggttcttc gagtcctggc caaagatgag aagcagcttt cacttctcgg ggatctggag     180
ggcctgaaac cccagaaggt ggacttctgg cgtggcccag ccaggcccag cctccctgtg     240
gatatgagag ttccttctc tgaactgaaa gacatcaaag cttatctgga gtctcatgga     300
cttgcttaca gcatcatgat aaaggacatc caggtgctgc tggatgagga agacaggcc     360 atggcgaaat cccgccggct ggagcgcagc accaacagct tcagttactc atcataccac     420
accctggagg agatatatag ctggattgac aactttgtaa tggagcattc cgatattgtc     480
tcaaaaattc agattggcaa cagctttgaa accagtcca ttcttgtcct gaagttcagc      540
actggaggtt ctcggcaccc agccatctgg atcgacactg gaattcactc ccgggagtgg     600
atcacccatg ccaccggcat ctggactgcc aataagaacc gcttatggcg aagaacaag     660 tccatcagac ctggaatctt ctgcatcggc gtggatctca acaggaactg gaagtcgggt    720
tttggaggaa atggttctaa cagcaaccc tgctcagaaa cttatcacgg ccctcccct    780 cagtcggagc ggaggtggc tgccatagtg aacttcatca cagcccatgg caacttcaag     840
gctctgatct ccatccacag ctactctcag atgcttatgt acccttacgg ccgattgctg     900
gagcccgttt caaatcagag ggagttgtac gatcttgcca aggatgcggt ggaggccttg    960
tataaggtcc atgggatcga gtacattttt ggcagcatca gcaccaccct ctatgtggcc    1020
agtgggatca ccgtcgactg ggcctatgac agtggcatca agtacgcctt cagctttgag    1080
ctccgggaca ctgggcagta tggcttcctg ctgccggcca cagatcat cccacggcc      1140 caggagacgt ggatggcgct tcggaccatc atggagcaca ccctgaatca ccctactag    1200

<210> SEQ ID NO 8
<211> LENGTH: 399
<212> TYPE: PRT
<213> ORGANISM: homo sapiens

<400> SEQUENCE: 8

Met Gln Gly Thr Pro Gly Gly Gly Thr Arg Pro Gly Pro Ser Pro Val
1               5                   10                  15

Asp Arg Arg Thr Leu Leu Val Phe Ser Phe Ile Leu Ala Ala Ala Leu
                20                  25                  30

Gly Gln Met Asn Phe Thr Gly Asp Gln Val Leu Arg Val Leu Ala Lys
            35                  40                  45

Asp Glu Lys Gln Leu Ser Leu Leu Gly Asp Leu Glu Gly Leu Lys Pro
        50                  55                  60
```

```
Gln Lys Val Asp Phe Trp Arg Gly Pro Ala Arg Pro Ser Leu Pro Val
 65                  70                  75                  80

Asp Met Arg Val Pro Phe Ser Glu Leu Lys Asp Ile Lys Ala Tyr Leu
                 85                  90                  95

Glu Ser His Gly Leu Ala Tyr Ser Ile Met Ile Lys Asp Ile Gln Val
            100                 105                 110

Leu Leu Asp Glu Arg Gln Ala Met Ala Lys Ser Arg Arg Leu Glu
        115                 120                 125

Arg Ser Thr Asn Ser Phe Ser Tyr Ser Tyr His Thr Leu Glu Glu
    130                 135                 140

Ile Tyr Ser Trp Ile Asp Asn Phe Val Met Glu His Ser Asp Ile Val
145                 150                 155                 160

Ser Lys Ile Gln Ile Gly Asn Ser Phe Glu Asn Gln Ser Ile Leu Val
                165                 170                 175

Leu Lys Phe Ser Thr Gly Gly Ser Arg His Pro Ala Ile Trp Ile Asp
            180                 185                 190

Thr Gly Ile His Ser Arg Glu Trp Ile Thr His Ala Thr Gly Ile Trp
            195                 200                 205

Thr Ala Asn Lys Asn Arg Leu Trp Arg Lys Asn Lys Ser Ile Arg Pro
210                 215                 220

Gly Ile Phe Cys Ile Gly Val Asp Leu Asn Arg Asn Trp Lys Ser Gly
225                 230                 235                 240

Phe Gly Gly Asn Gly Ser Asn Ser Asn Pro Cys Ser Glu Thr Tyr His
                245                 250                 255

Gly Pro Ser Pro Gln Ser Glu Pro Glu Val Ala Ala Ile Val Asn Phe
            260                 265                 270

Ile Thr Ala His Gly Asn Phe Lys Ala Leu Ile Ser Ile His Ser Tyr
            275                 280                 285

Ser Gln Met Leu Met Tyr Pro Tyr Gly Arg Leu Leu Glu Pro Val Ser
    290                 295                 300

Asn Gln Arg Glu Leu Tyr Asp Leu Ala Lys Asp Ala Val Glu Ala Leu
305                 310                 315                 320

Tyr Lys Val His Gly Ile Glu Tyr Ile Phe Gly Ser Ile Ser Thr Thr
                325                 330                 335

Leu Tyr Val Ala Ser Gly Ile Thr Val Asp Trp Ala Tyr Asp Ser Gly
            340                 345                 350

Ile Lys Tyr Ala Phe Ser Phe Glu Leu Arg Asp Thr Gly Gln Tyr Gly
            355                 360                 365

Phe Leu Leu Pro Ala Thr Gln Ile Ile Pro Thr Ala Gln Glu Thr Trp
    370                 375                 380

Met Ala Leu Arg Thr Ile Met Glu His Thr Leu Asn His Pro Tyr
385                 390                 395

<210> SEQ ID NO 9
<211> LENGTH: 1056
<212> TYPE: DNA
<213> ORGANISM: homo sapiens

<400> SEQUENCE: 9
atgcaggcca cccctggagg cgggacgcgc cctgggccat ccccgtgga caggcggaca      60 ctcctggtct tcagctttat cctggcagca gctttgggcc aaatgaattt cacaggggac    120
caggttcttc gagtcctggc caaagatgag aagcagcttt cacttctcgg ggatctggag    180
ggcctgaaac cccagaaggt ggacttctgg cgtggcccag ccaggcccag cctccctgtg    240
```

```
                                                              -continued gatatgagag ttcctttctc tgaactgaaa gacatcaaag cttatctgga gtctcatgga      300
cttgcttaca gcatcatgat aaaggacatc caggtgctgc tggatgagga agacaggcc      360 atggcgaaat cccgccggct ggagcgcagc accaacagct tcagttactc atcataccac      420
accctggagg agatatatag ctggattgac aactttgtaa tggagcattc cgatattgtc      480
tcaaaaattc agattggcaa cagctttgaa accagtcca ttcttgtcct gaagttcagc      540
actggaggtt ctcggcaccc agccatctgg atcgacactg gaattcactc ccgggagtgg      600
atcacccatg ccaccggcat ctggactgcc aataagattg tcagtgatta tggcaaagac      660
cgtgtcctga cagacatact gaatgccatg gacatcttca tagagctcgt cacaaacccct     720 gatgggtttg cttttaccca cagcatgaac cgcttatggc ggaagaacaa gtccatcaga      780
cctggaatct tctgcatcgg cgtggatctc aacaggaact ggaagtcggg ttttggagga      840
aatggttcta acagcaaccc ctgctcagaa acttatcacg gccctcccc tcagtcggag      900 ccggaggtgg ctgccatagt gaacttcatc acagcccatg caacttcaa ggctctgatc      960 tccatccaca gctactctca gatgcttatg taccctacg gccgattgct ggagcccgtt     1020
tcaaatcaga gggagttggt gagactggct gcttag                              1056

<210> SEQ ID NO 10
<211> LENGTH: 351
<212> TYPE: PRT
<213> ORGANISM: homo sapiens

<400> SEQUENCE: 10

Met Gln Gly Thr Pro Gly Gly Thr Arg Pro Gly Pro Ser Pro Val
 1               5                  10                  15

Asp Arg Arg Thr Leu Leu Val Phe Ser Phe Ile Leu Ala Ala Ala Leu
             20                  25                  30

Gly Gln Met Asn Phe Thr Gly Asp Gln Val Leu Arg Val Leu Ala Lys
         35                  40                  45

Asp Glu Lys Gln Leu Ser Leu Leu Gly Asp Leu Glu Gly Leu Lys Pro
     50                  55                  60

Gln Lys Val Asp Phe Trp Arg Gly Pro Ala Arg Pro Ser Leu Pro Val
65                  70                  75                  80

Asp Met Arg Val Pro Phe Ser Glu Leu Lys Asp Ile Lys Ala Tyr Leu
                 85                  90                  95

Glu Ser His Gly Leu Ala Tyr Ser Ile Met Ile Lys Asp Ile Gln Val
            100                 105                 110

Leu Leu Asp Glu Glu Arg Gln Ala Met Ala Lys Ser Arg Arg Leu Glu
        115                 120                 125

Arg Ser Thr Asn Ser Phe Ser Tyr Ser Ser Tyr His Thr Leu Glu Glu
    130                 135                 140

Ile Tyr Ser Trp Ile Asp Asn Phe Val Met Glu His Ser Asp Ile Val
145                 150                 155                 160

Ser Lys Ile Gln Ile Gly Asn Ser Phe Glu Asn Gln Ser Ile Leu Val
                165                 170                 175

Leu Lys Phe Ser Thr Gly Gly Ser Arg His Pro Ala Ile Trp Ile Asp
            180                 185                 190

Thr Gly Ile His Ser Arg Glu Trp Ile Thr His Ala Thr Gly Ile Trp
        195                 200                 205

Thr Ala Asn Lys Ile Val Ser Asp Tyr Gly Lys Asp Arg Val Leu Thr
    210                 215                 220
```

```
Asp Ile Leu Asn Ala Met Asp Ile Phe Ile Glu Leu Val Thr Asn Pro
225                 230                 235                 240

Asp Gly Phe Ala Phe Thr His Ser Met Asn Arg Leu Trp Arg Lys Asn
                245                 250                 255

Lys Ser Ile Arg Pro Gly Ile Phe Cys Ile Gly Val Asp Leu Asn Arg
                260                 265                 270

Asn Trp Lys Ser Gly Phe Gly Gly Asn Gly Ser Asn Ser Asn Pro Cys
            275                 280                 285

Ser Glu Thr Tyr His Gly Pro Ser Pro Gln Ser Glu Pro Glu Val Ala
        290                 295                 300

Ala Ile Val Asn Phe Ile Thr Ala His Gly Asn Phe Lys Ala Leu Ile
305                 310                 315                 320

Ser Ile His Ser Tyr Ser Gln Met Leu Met Tyr Pro Tyr Gly Arg Leu
                325                 330                 335

Leu Glu Pro Val Ser Asn Gln Arg Glu Leu Val Arg Leu Ala Ala
                340                 345                 350

<210> SEQ ID NO 11
<211> LENGTH: 945
<212> TYPE: DNA
<213> ORGANISM: homo sapiens

<400> SEQUENCE: 11 atgcaggca  cccctggagg  cgggacgcgc  cctgggccat  ccccgtgga  caggcggaca      60 ctcctggtct  tcagctttat  cctggcagca  gctttgggcc  aaatgaattt  cacaggggac    120
caggttcttc  gagtcctggc  caaagatgag  aagcagcttt  cacttctcgg  ggatctggag    180
ggcctgaaac  cccagaaggt  ggacttctgg  cgtggcccag  ccaggcccag  cctccctgtg    240
gatatgagag  ttcctttctc  tgaactgaaa  gacatcaaag  cttatctgga  gtctcatgga    300
cttgcttaca  gcatcatgat  aaaggacatc  caggtgctgc  tggatgagga  agacaggcc     360 atggcgaaat  cccgccggct  ggagcgcagc  accaacagct  tcagttactc  atcataccac    420
accctggagg  agatatatag  ctggattgac  aactttgtaa  tggagcattc  cgatattgtc    480
tcaaaaattc  agattggcaa  cagctttgaa  accagtccca  ttcttgtcct  gaagttcagc    540
actggaggtt  ctcggcaccc  agccatctgg  atcgacactg  gaattcactc  ccgggagtgg    600
atcacccatg  ccaccggcat  ctggactgcc  aataagaacc  gcttatggcg  gaagaacaag    660
tccatcagac  tggaatcttc  tgcatcggc  gtggatctca  acaggaactg  gaagtcgggt    720
tttggaggaa  atggttctaa  cagcaaccc  tgctcagaaa  cttatcacgg  gccctcccct    780
cagtcggagc  cggaggtggc  tgccatagtg  aacttcatca  cagcccatgg  caacttcaag    840
gctctgatct  ccatccacag  ctactctcag  atgcttatgt  accttacgg  ccgattgctg    900 gagcccgttt  caaatcagag  ggagttggtg  agactggctg  cttag                     945

<210> SEQ ID NO 12
<211> LENGTH: 314
<212> TYPE: PRT
<213> ORGANISM: homo sapiens

<400> SEQUENCE: 12

Met Gln Gly Thr Pro Gly Gly Gly Thr Arg Pro Gly Pro Ser Pro Val
  1               5                  10                  15

Asp Arg Arg Thr Leu Leu Val Phe Ser Phe Ile Leu Ala Ala Ala Leu
                 20                  25                  30

Gly Gln Met Asn Phe Thr Gly Asp Gln Val Leu Arg Val Leu Ala Lys
```

-continued

```
                35                  40                  45
Asp Glu Lys Gln Leu Ser Leu Leu Gly Asp Leu Glu Gly Leu Lys Pro
    50                  55                  60
Gln Lys Val Asp Phe Trp Arg Gly Pro Ala Arg Pro Ser Leu Pro Val
65                  70                  75                  80
Asp Met Arg Val Pro Phe Ser Glu Leu Lys Asp Ile Lys Ala Tyr Leu
                85                  90                  95
Glu Ser His Gly Leu Ala Tyr Ser Ile Met Ile Lys Asp Ile Gln Val
            100                 105                 110
Leu Leu Asp Glu Glu Arg Gln Ala Met Ala Lys Ser Arg Arg Leu Glu
        115                 120                 125
Arg Ser Thr Asn Ser Phe Ser Tyr Ser Ser Tyr His Thr Leu Glu Glu
    130                 135                 140
Ile Tyr Ser Trp Ile Asp Asn Phe Val Met Glu His Ser Asp Ile Val
145                 150                 155                 160
Ser Lys Ile Gln Ile Gly Asn Ser Phe Glu Asn Gln Ser Ile Leu Val
                165                 170                 175
Leu Lys Phe Ser Thr Gly Gly Ser Arg His Pro Ala Ile Trp Ile Asp
            180                 185                 190
Thr Gly Ile His Ser Arg Glu Trp Ile Thr His Ala Thr Gly Ile Trp
        195                 200                 205
Thr Ala Asn Lys Asn Arg Leu Trp Arg Lys Asn Lys Ser Ile Arg Pro
    210                 215                 220
Gly Ile Phe Cys Ile Gly Val Asp Leu Asn Arg Asn Trp Lys Ser Gly
225                 230                 235                 240
Phe Gly Gly Asn Gly Ser Asn Ser Asn Pro Cys Ser Glu Thr Tyr His
                245                 250                 255
Gly Pro Ser Pro Gln Ser Glu Pro Glu Val Ala Ala Ile Val Asn Phe
            260                 265                 270
Ile Thr Ala His Gly Asn Phe Lys Ala Leu Ile Ser Ile His Ser Tyr
        275                 280                 285
Ser Gln Met Leu Met Tyr Pro Tyr Gly Arg Leu Leu Glu Pro Val Ser
    290                 295                 300
Asn Gln Arg Glu Leu Val Arg Leu Ala Ala
305                 310
```

<210> SEQ ID NO 13
<211> LENGTH: 210
<212> TYPE: DNA
<213> ORGANISM: homo sapiens

<400> SEQUENCE: 13

```
atgatgtttt tgaacaagaa gacrccccat gggtgctgtg ctgtcctgag cctgggcca    60
tggtgcccaa ggaaagcccc tgaagctcac caggaggaag aagcatgcag ggcacccctg   120
gaggcgggac gcgccctggg ccatcccccg tggacaggcg acactcctg gtcttcagct    180
ttatcctggc agcagctttg ggccaaatga                                    210
```

<210> SEQ ID NO 14
<211> LENGTH: 69
<212> TYPE: PRT
<213> ORGANISM: homo sapiens

<400> SEQUENCE: 14

```
Met Met Phe Leu Asn Lys Lys Thr Pro His Gly Cys Cys Ala Val Leu
1               5                   10                  15
```

Arg Pro Gly Pro Trp Cys Pro Arg Lys Ala Pro Glu Ala His Gln Glu
        20                  25                  30

Glu Glu Ala Cys Arg Ala Pro Leu Glu Ala Gly Arg Ala Leu Gly His
    35                  40                  45

Pro Pro Trp Thr Gly Gly His Ser Trp Ser Ser Ala Leu Ser Trp Gln
    50                  55                  60

Gln Leu Trp Ala Lys
65

<210> SEQ ID NO 15
<211> LENGTH: 2247
<212> TYPE: DNA
<213> ORGANISM: homo sapiens

<400> SEQUENCE: 15

| | | | | | |
|---|---|---|---|---|---|
| ctctctctct | cttttactct | tactctttct | ctctcactct | ctctcttttc | ccacccttaa | 60 |
| gccaagtaca | gggatagttg | tctcatcatt | ggtggcttaa | aatgatgttt | ttgaacaaga | 120 |
| agacrcccca | tgggtacttt | tggtgactag | cactatctct | gtkttttttcc | ttttaaattc | 180 |
| ctgagctatt | gtttagcagt | acacccttt | atctccattg | ctactgaagc | tgaatgttac | 240 |
| ttgggtggaa | agcataactg | ctttcttttc | tatgtcctta | aacccttttga | taatgttact | 300 |
| gtttgagagt | ccctgaagcc | aggatactag | aagagtctgg | cttgtctgaa | cagctgaact | 360 |
| acgaaataat | ggagtagggc | aggctttacc | aagccaattc | actcaagttg | tctcatctat | 420 |
| accccttcaa | accctgtgag | ctgtgactaa | aagctgggct | ttccagcctc | taggtgctgt | 480 |
| gctgtcctga | ggcctgggcc | atggtgccca | aggaaagccc | ctgaagctca | ccaggaggaa | 540 |
| gaagcatgca | gggcacccct | ggaggcggga | cgcgccctgg | gccatccccc | gtggacaggc | 600 |
| ggacactcct | ggtcttcagc | tttatcctgg | cagcagcttt | gggccaaatg | aatttcacag | 660 |
| gggaccaggt | tcttcgagtc | ctggccaaag | atgagaagca | gctttcactt | ctcggggatc | 720 |
| tggagggcct | gaaaccccag | aagtggact | tctggcgtgg | cccagccagg | cccagcctcc | 780 |
| ctgtggatat | gagagttcct | ttctctgaac | tgaaagacat | caaagcttat | ctggagtctc | 840 |
| atggacttgc | ttacagcatc | atgataaagg | acatccaggt | gctgctggat | gaggaaagac | 900 |
| aggccatggc | gaaatcccgc | cggctggagc | gcagcaccaa | cagcttcagt | tactcatcat | 960 |
| accacaccct | ggaggagata | tatagctgga | ttgacaactt | tgtaatggag | cattccgata | 1020 |
| ttgtctcaaa | aattcagatt | ggcaacagct | ttgaaaacca | gtccattctt | gtcctgaagt | 1080 |
| tcagcactgg | aggttctcgg | cacccagcca | tctggatcga | cactggaatt | cactcccggg | 1140 |
| agtggatcac | ccatgccacc | ggcatctgga | ctgccaataa | gattgtcagt | gattatggca | 1200 |
| aagaccgtgt | cctgacagac | atactgaatg | ccatggacat | cttcatagag | ctcgtcacaa | 1260 |
| accctgatgg | gtttgctttt | acccacagca | tgaaccgctt | atggcggaag | aacaagtcca | 1320 |
| tcagacctgg | aatcttctgc | atcggcgtgg | atctcaacag | gaactggaag | tcgggttttg | 1380 |
| gaggaaatgg | ttctaacagc | aaccctgct | cagaaactta | tcacgggccc | tcccctcagt | 1440 |
| cggagccgga | ggtggctgcc | atagtgaact | tcatcacagc | ccatggcaac | ttcaaggctc | 1500 |
| tgatctccat | ccacagctac | tctcagatgc | ttatgtaccc | ttacgccga | ttgctggagc | 1560 |
| ccgtttcaaa | tcagagggag | ttggtgagac | tggctgctta | gggcctgggg | agaagagacc | 1620 |
| gcttcacaga | aaaatccata | tctgtcatac | tcccagaggg | ctcaggttgt | tactctgaat | 1680 |
| gcagggtct | gggctgattg | accccatggt | gcgggggtg | gggtaggggg | agcttgctgt | 1740 |

-continued

| | | | | |
|---|---|---|---|---|
| tctcacgtgt | gatcaagttc | aaagctggaa | atgctgtgct | ccttctcaca agggccatct | 1800 |
| cacttcaact | tcaggactgc | taaatcatgc | ttacgatctt | gccaaggatg cggtggaggc | 1860 |
| cttgtataag | gtccatggga | tcgagtacat | ttttggcagc | atcagcacca ccctctatgt | 1920 |
| ggccagtggg | atcaccgtcg | actgggccta | tgacagtggc | atcaagtacg ccttcagctt | 1980 |
| tgagctccgg | gacactgggc | agtatggctt | cctgctgccg | gccacacaga tcatccccac | 2040 |
| ggcccaggag | acgtggatgg | cgcttcggac | catcatggag | cacaccctga atcaccccta | 2100 |
| ctagcagcac | gactgagggc | aggaggctcc | atccttctcc | ccaaggtctg tggctcctcc | 2160 |
| cgaaacccaa | gttatgcatc | cccatcccca | tgccctcatc | ccgacctctt agaaaataaa | 2220 |
| tacaagtttg | aaaaaaaaaa | aaaaaaa | | | 2247 |